United States Patent [19]

Bonaccorsi et al.

[11] Patent Number: 5,089,577
[45] Date of Patent: Feb. 18, 1992

[54] POLYMERS AND COPOLYMERS CONTAINING MALONIC (METH)ACRYLAMIDE UNITS

[75] Inventors: Fabrizio Bonaccorsi, Livorno; Rosario Pappa; Mario Riocci, both of Monterotondo; Arnaldo Roggero; Thomas P. Lockhart, both of San Donato Milanese, all of Italy

[73] Assignee: Eniricerche S.p.A. and AGIP S.p.A., Milan, Italy

[21] Appl. No.: 629,409

[22] Filed: Dec. 18, 1990

[30] Foreign Application Priority Data

Dec. 21, 1989 [IT] Italy .................. 22799 A/89

[51] Int. Cl.$^5$ .............................. C08F 22/38
[52] U.S. Cl. ........................... 526/240; 526/304
[58] Field of Search .................... 526/240, 304

[56] References Cited

U.S. PATENT DOCUMENTS 4,289,676  9/1981  Czauderna .............. 526/304 X

FOREIGN PATENT DOCUMENTS 57-14673  1/1982  Japan .
1068037   5/1967  United Kingdom .
1310613   3/1973  United Kingdom .

Primary Examiner—Joseph L. Schofer
Assistant Examiner—M. Nagumo
Attorney, Agent, or Firm—Hedman, Gibson & Costigan

[57] ABSTRACT

New homopolymers formed by malonic (meth)acrylamide monomer units according to the following formula:

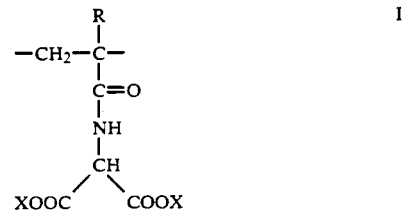

wherein R is H or $CH_3$; X is H or an alkaline metal or $NH_4^+$; and copolymers formed by (meth)acrylamide monomer units (I) and monomer units (II).

10 Claims, No Drawings

POLYMERS AND COPOLYMERS CONTAINING MALONIC (METH)ACRYLAMIDE UNITS

This invention concerns new homopolymers formed by malonic (meth)acrylamide monomers of the following formula:

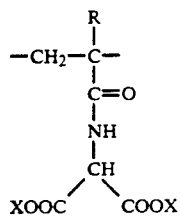

wherein R is H or $CH_3$; X is H or alkaline metal, preferably sodium or potassium, or is $NH_4^+$; and copolymers formed by (meth)acrylamide monomer units (I) and monomer units (II), the molar ratio between units (I) and units (II) varying between 1:99 and 99:1.

Acrylamide-type polymers are known in the art, said polymers containing units bearing radicals of monocarboxylic acids or hydroxylated alkyl radicals, linked with the amide nitrogen.

As an example, English Patent GB1310613 describes homopolymers formed by units of N-carboxymerhyl acrylamide or N,N di(carboxy methyl) acrylamide, useful to prevent the deposit of insoluble salts, particularly calcium salts on surfaces in contact with hot aqueous solutions. On the other hand, Patent GB1068037 describes copolymers having divalent and polyvalent metal-complexing properties, containing either units bearing N-carboxymethyl amides or N,N-dicarboxymethyl amides or units bearing N-hydroxyethyl amide groups.

With this invention, new and effective polymers have been found, featuring the presence in the polymer chain of units responding to formula I, bearing a bicarboxylic acid radical linked with the amide nitrogen, viz. malonic acid.

Such polymers, being homopolymers formed exclusively of formula I units or copolymers with (meth)acrylamide, can be effectively used in various sectors.

As an example they may be used advantageously in water treatment, to eliminate and/or recover metals or to inhibit the formation of incrustations due to deposits of insoluble salts, for instance calcium salts.

For that purpose those copolymers are used preferably with a molar ratio between formula (I) monomer units and (meth)acrylamide monomer (II) units which varies between 70:30 and 99:1.

Copolymers in this invention may also be used with flocculants to precipitate solids in aqueous suspension. Copolymers are then used preferably with a molar ratio of (I):(II) between 1:99 and 30:70.

These may also be used in the paperboard industry and as components of adhesive mixtures.

Both homopolymers and copolymers in this invention are water-soluble even in very high concentrations having an weight average molecular weight varying between 1000 and 20,000,000 preferably 1,000,000 to 10,000,000. These may be prepared by homopolymerisation of monomers according to the following formula:

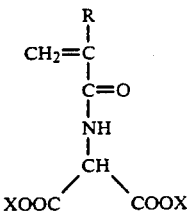

wherein: R is H or $CH_3$; X is H or an alkaline metal or $NH_4$;

or in the case of copolymers, by copolymerisation of the above monomers with (meth)acrylamide, using the radical polymerisation methods known in present technique. Polymerisation may generally be effected by operating in solution, emulsion or suspension, and is preferably achieved in solution.

An aqueous solution is used in practice, with a pH going from 2 to 10 approximately, using radical initiators, for instance peroxides, persulphates or nitrogen compounds.

Homopolymers and copolymers in which X is alkaline metal or $NH_4^+$, may be obtained by polymerising relevant formula III monomers in which X is an alkaline metal or $NH_4^+$, or by polymerising the monomer in the acid form (X=H) and adding to the final polymer solution the inorganic base adapted to obtain the required salt, for instance NaOH, KOH or $NH_4OH$.

In the same manner the copolymers in which X=H can be obtained by polymerising the relevant formula II monomer wherein X=H or by polymerising the monomer in salt form (X=alkaline metal, $NH_4^+$) then acidifying the polymer final solution, adding hydrochloric acid or sulphuric acid for instance.

The temperature of the copolymerisation reaction may generally vary between ambient temperature (15°-25° C.) and 90° C. approximately and conversion of the monomers is practically completed within a period of 30 minutes to 24 hours depending on the temperature used, usual procedure generally featuring a 50°-70° temperature for a period of 1-2 hours.

The molar ratio of the monomers thus introduced is also maintained unchanged in the final copolymer. Monomers complying with formula (II), used to produce polymers according to the present invention, are new and may be obtained quite simply according to known organic chemistry methodology.

For example they are prepared by the reaction of 2-amino diethyl malonate dissolved in aqueous inorganic base, for example sodium hydroxyde, with acryloyl chloride or metacryloyl chloride, adding the chloride at low temperature, around 5° C., in the presence of polymerisation inhibitors, such as 3-methoxy phenol. The reaction occurs at ambient temperature and a high product yield is achieved.

The following examples are for information purposes, and are not to be considered restrictive of the scope of the invention.

EXAMPLE 1

Preparation of 2-acrylamide malonic acid (as in formula I:R, X=H).

10,5 g (0,05 moles) of 2-amino diethyl malonate are dissolved in 200 ml of 2N NaOH containing 50 mg of 3-methoxy phenol, a polymerisation inhibitor.

3,75 g (0,152 moles) of acryloyl chloride are then slowly added to the solution protected against the light and cooled to 5° C.

On completion of the addition, the solution thus obtained is then kept stirred for one hour at ambient temperature, and on completion, extracted with ethyl acetate to remove any non-reacted acryloyl chloride. The aqueous phase, containing the bisodium 2-acrylamide malonic acid salt, is then passed over a column charged with a cationic resin DOWEX H+ 50X8 to convert the product into the acid form and exclude excess soda.

The fractions containing the product are then freeze-dried, thus obtaining 7.5 g of 2-acrylamide malonic acid, which represents an 87% yield. Product structure was confirmed by $^1$HNMR spectroscopy and mass spectrometer analyses.

EXAMPLE 2

Using a 500 ml reactor with mechanical stirrer and condenser, 20 g (0,115 moles) of malonic 2-acrylamide acid and 200 ml of de-ionised water are added, and the pH is adjusted to pH 9 with a 2N soda addition. The resulting solution is placed under nitrogen flow for 2 hours to eliminate any contained air; on completion it is heated to 60° and a slow addition is made of a solution of 31,1 mg (0,115 mmoles) of $K_2S_2O_8$ in 5 ml of de-ionised water.

The mixture is then left to react 90 minutes at 60° C. It is finally cooled to ambient temperature, then diluted with de-ionised water and the polymer obtained in sodium salt form (as in formula I:X=Na) is recovered and purified by two successive precipitations with the addition of methanol at pH 10.

There are obtained, upon drying under reduced pressure, 18 g of poly(sodium (2-acrylamido)malonate), corresponding to a 90% conversion. The homopolymer weight average molecular weight thus obtained (assessed by GPC) is 2,700,000 g/mole.

EXAMPLE 3

In a 500 ml reactor with mechanical stirrer and condenser, add 20 g (0,282 moles) of acrylamide, 1,50 g (0,0087 moles) of 2-acrylamide malonic acid (equal to 97:3 molar ratio of acrylamide:2-acrylamide malonic acid), 200 ml of de-ionised water, then adding soda to adjust the pH to 9.

The mixture is placed under nitrogen flow to remove any contained air; on completion it is heated to 60° C. A solution of 78,4 mg (0,29 mmoles) of $K_2S_2O_8$ in 5 ml of de-ionised water is quickly added and the reaction is allowed to continue for 75 minutes, the temperature being maintained at 60° C.

On completion the mixture thus obtained is cooled to ambient temperature and the polymer is recovered and refined with two successive precipitations using methanol at pH 10.

After drying under low pressure 20,7 g of copolymers are obtained representing a practically complete conversion of the monomers. The molar ratio between acrylamide and 2-acrylamide malonic acid units (in the form of bisodium salt) assessed by $^{13}$CNMR spectroscope analyses, was 97,1:2,9.

The copolymer properties obtained were as follows:
Weight average molecular weight (GPC): 3,300,000 g/mole Intrinsic viscosity (in aqueous 2M NaCl solution at 25° C.): 802 cm$^3$/g

EXAMPLE 4

The procedure is as in example 3, with the exception that polymerisation is effected with a pH of 4, adding hydrochloric acid to the initial solution and the copolymer being recovered on completion by means of an addition of methanol at an acid pH.

The monomer conversion rate is around 95% and the molar ratio between malonic acrylamide units and acrylamide units is practically equal with the input. The copolymer properties were as follows Weight average molecular weight: 3,400,000 g/mole
Intrinsic viscosity: 795 cm$^3$/g

EXAMPLE 5

The procedure is as described in example 3, with the exception that the input features a molar ratio of 2-acrylamide malonic acid: acrylamide representing 5:95 and that the polymerisation time is 1 hour.

The monomer conversion rate is around 90% and properties of the copolymer obtained are as follows:
Molar ratio between 2-acrylamide malonic units and acrylamide units: 5:95;

Weight average . molecular weight: 3,600,000 g/mole
Intrinsic viscosity: 802 cm$^3$/g

EXAMPLE 6

The procedure is as described in example 5, with the exception that the polymerisation is effected at pH 4. The copolymer is obtained in the form of sodium salt, by the addition of 2N NaOH to the final solution and precipitation with methanol.

The monomer conversion rate is around 90% and the properties of the copolymer obtained are as follows:
Molar ratio between 2-acrylamide malonic units and acrylamide units: 4,4:95,6

Weight average molecular weight: 3,900,000 g/mole
Intrinsic viscosity: 970 cm$^3$/g

We claim:

1. A homopolymer formed from monomers of the following general formula:

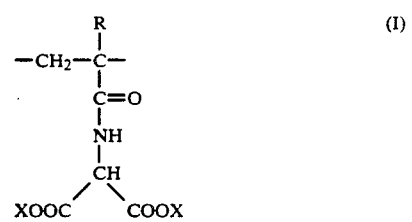

wherein R is H or $CH_3$; X is H or an alkaline metal, or $NH_4^+$.

2. A homopolymer as defined in claim 1 having a weight average molecular weight ranging from 1000 to 20,000,000.

3. A homopolymer as defined in claim 2 having a weight average molecular weight ranging from 1,000,000 to 20,000,000.

4. A homopolymer as defined in claim 1, wherein said alkaline metal is sodium or potassium.

5. A copolymer formed from (I) monomer units of the following general formula:

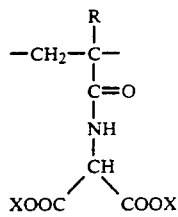

wherein R is H or CH₃; X is H or an alkaline metal, or NH₄⁺; and (II) units of carylamide or methacrylamide, the molar ratio of units (I) to units (II) ranging from between 1:99 to 99:1.

6. A copolymer as defined in claim 5 having a weight average molecular weight ranging from 1000 to 20,000,000.

7. A copolymer as defined in claim 6 having a weight average molecular weight ranging from 1,000,000 to 20,000,000.

8. A copolymer as defined in claim 5 wherein the molar ratio of units (I) to units (II) ranges from 70:30 to 99:1.

9. A copolymer as defined in claim 5, wherein the molar ratio of units (I) to units (II) ranges from 1:99 to 30:70.

10. A copolymer as defined in claim 5, wherein said alkaline metal is sodium or potassium.

* * * * *